United States Patent
Tewari et al.

(10) Patent No.: US 8,466,696 B2
(45) Date of Patent: Jun. 18, 2013

(54) SYSTEM AND METHOD FOR DETECTING A LIKELIHOOD OF CORROSION

(75) Inventors: Asim Tewari, Maharashtra (IN);
Deepika Sachdeva, Karnataka (IN);
Kiran Deshpande, Bangalore (IN);
Arun M. Kumar, Karnataka (IN);
Pulak Bandyopadhyay, Rochester Hills, MI (US); Jon T. Carter, Farmington, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 272 days.

(21) Appl. No.: 13/075,499

(22) Filed: Mar. 30, 2011

(65) Prior Publication Data

US 2012/0247975 A1 Oct. 4, 2012

(51) Int. Cl.
*G01R 27/08* (2006.01)

(52) U.S. Cl.
USPC .......................................................... 324/700

(58) Field of Classification Search
USPC .......................................................... 324/700
See application file for complete search history.

(56) References Cited

U.S. PATENT DOCUMENTS

| | | | | |
|---|---|---|---|---|
| 4,238,298 A * | 12/1980 | Tsuru et al. | ............... | 205/775.5 |
| 4,395,318 A * | 7/1983 | Tait et al. | ...................... | 204/404 |
| 4,831,324 A * | 5/1989 | Asakura et al. | ............... | 324/615 |
| 4,863,571 A * | 9/1989 | Chambaere | ................ | 205/776.5 |
| 5,006,786 A * | 4/1991 | McKubre et al. | .......... | 205/775.5 |
| 5,126,654 A * | 6/1992 | Murphy et al. | ............... | 324/71.2 |
| 5,139,627 A * | 8/1992 | Eden et al. | ................. | 205/775.5 |
| 5,286,357 A * | 2/1994 | Smart et al. | ................... | 205/776 |
| 5,425,867 A * | 6/1995 | Dawson et al. | ............... | 204/400 |
| 5,865,971 A * | 2/1999 | Sunkara | ........................ | 204/404 |
| 7,295,131 B2 * | 11/2007 | Anderson et al. | ............ | 340/679 |
| 7,634,392 B2 * | 12/2009 | Kwun et al. | ...................... | 703/5 |
| 8,285,495 B2 * | 10/2012 | Purekar et al. | .................. | 702/39 |
| 2004/0178790 A1 * | 9/2004 | Gifford et al. | ................. | 324/242 |
| 2005/0263395 A1 * | 12/2005 | Nielsen et al. | ................. | 204/408 |
| 2006/0152380 A1 * | 7/2006 | Anderson et al. | ............ | 340/679 |
| 2012/0247975 A1 * | 10/2012 | Tewari et al. | ............... | 205/775.5 |

* cited by examiner

*Primary Examiner* — Jermele M Hollington
*Assistant Examiner* — Demetrius Pretlow
(74) *Attorney, Agent, or Firm* — Quinn Law Group, PLLC

(57) ABSTRACT

A system may be used to detect corrosion between a first metal and a second metal, where the second metal is positioned adjacent to the first metal. The system may include a processor electrically coupled to each of the first and the second metals and configured to monitor a complex impedance between the first metal and the second metal, where the complex impedance may include a real component and an imaginary component. The processor may compare the real component of the complex impedance to a first threshold, compare the imaginary component of the complex impedance to a second threshold, and indicate a likelihood of corrosion if at least one of the real and imaginary components are below their respective threshold.

20 Claims, 2 Drawing Sheets

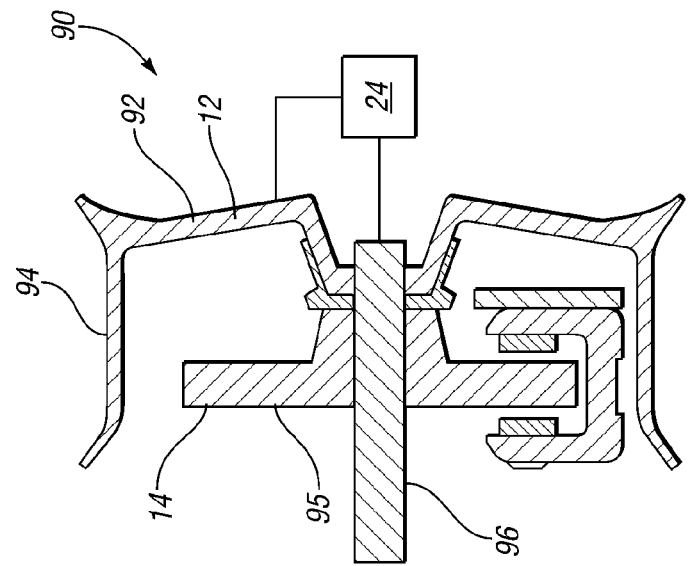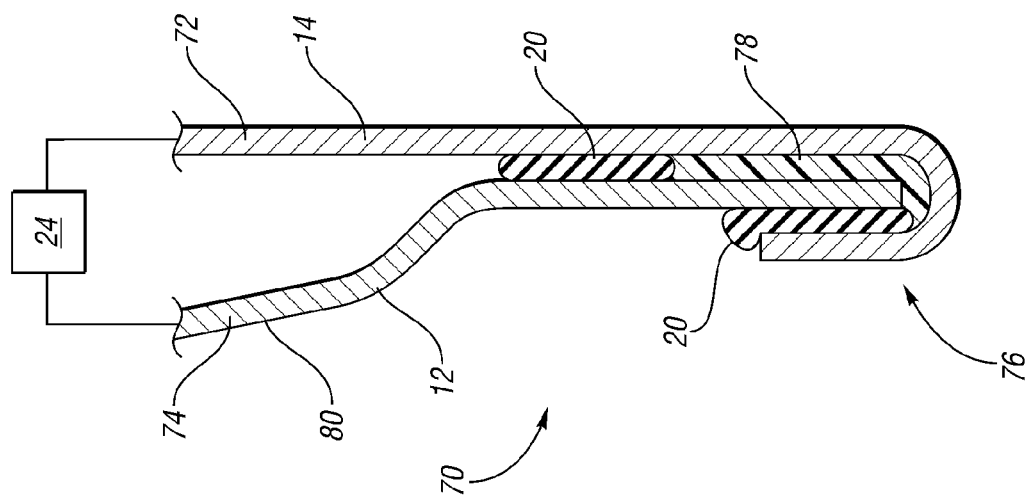

SYSTEM AND METHOD FOR DETECTING A LIKELIHOOD OF CORROSION

TECHNICAL FIELD

The present invention relates generally to systems and methods for detecting a likelihood of corrosion.

BACKGROUND

Within the metallurgical arts, many types of corrosion may exist. Galvanic corrosion is a particular form of corrosion characterized by an electrochemical process in which one metal corrodes preferentially to another metal. For galvanic corrosion to exist, both metals must be in electrical contact and immersed in an electrolyte. Such a configuration is often referred to as a "galvanic couple" and results when each metal has a different electrode potential. Various metals are often ranked according to their electrode potential in the "Anodic Index," with magnesium having a generally higher potential than steel, steel having a generally higher potential than copper, and gold having the lowest potential.

In a galvanic couple, the electrolyte provides a means for transport of metallic ions and the electrical contact ensures migration of electrons from the more anodic metal to the less anodic metal (i.e., the more cathodic metal). This leads to the anodic metal corroding more quickly than it otherwise would, while the corrosion of the cathodic metal is retarded even to the point of stopping.

Alternative modes of corrosion may include crevice corrosion, and/or pitting corrosion. In crevice and pitting corrosion, for example, a pseudo-galvanic couple is achieved between two regions of a single piece of metal. For example, the polarization of the metal within the crevice may be altered by the presence of a stagnant electrolyte. This altered potential may, for example, serve as the anode and corrode preferentially to the remainder of the metal, which may be more cathodic.

SUMMARY

A system may be used to detect corrosion between a first metal and a second metal, where the second metal is positioned adjacent to the first metal. The system may include a processor electrically coupled to each of the first and the second metals and configured to monitor a complex impedance between the first metal and the second metal, where the complex impedance may include a real component and an imaginary component. The processor may compare the real component of the complex impedance to a first threshold, compare the imaginary component of the complex impedance to a second threshold, and indicate a likelihood of corrosion if at least one of the real and imaginary components is below its respective threshold. In an embodiment, the system may be implemented within an automotive vehicle and may, for example, indicate a likelihood of corrosion between two metals disposed in a hemmed arrangement, or in a vehicle wheel.

The processor may be configured to indicate the presence of an electrolytic solution in contact with the first and second metals if the imaginary component of the monitored complex impedance is below the second threshold. Furthermore, in a system that is provided with an electrically insulating material between the first metal and the second metal, the processor may be configured to indicate damage to the insulating material if the real component of the monitored complex impedance is below the first threshold.

The processor may further be capable of taking remedial action to remove the electrolytic solution if the presence of the solution is indicated. Such remedial action may include energizing a resistive heating element located proximate to the first and second metals to evaporate the solution. Likewise, the processor may indicate damage to the insulating material by storing a diagnostic trouble code in a memory of an on board computer provided within the vehicle.

Additionally, a method of detecting a likelihood of corrosion between a first metal and a second metal may include monitoring a complex impedance between the first and second metals, where the complex impedance includes a real component and an imaginary component. Subsequently, the method may include comparing the real component of the complex impedance to a first threshold, comparing the imaginary component of the complex impedance to a second threshold; and indicating a likelihood of corrosion if at least one of the real and imaginary components is below their respective threshold. The method may further include taking remedial action to remove the electrolytic solution if the presence of the solution is indicated.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 3 is a schematic cross-sectional illustration of a system for indicating a likelihood of corrosion between two panels in a hemmed closure arrangement.

FIG. 4 is a schematic illustration of a system for indicating a likelihood of corrosion between a wheel and an axle in an automotive wheel assembly.

DETAILED DESCRIPTION

Figure 1:
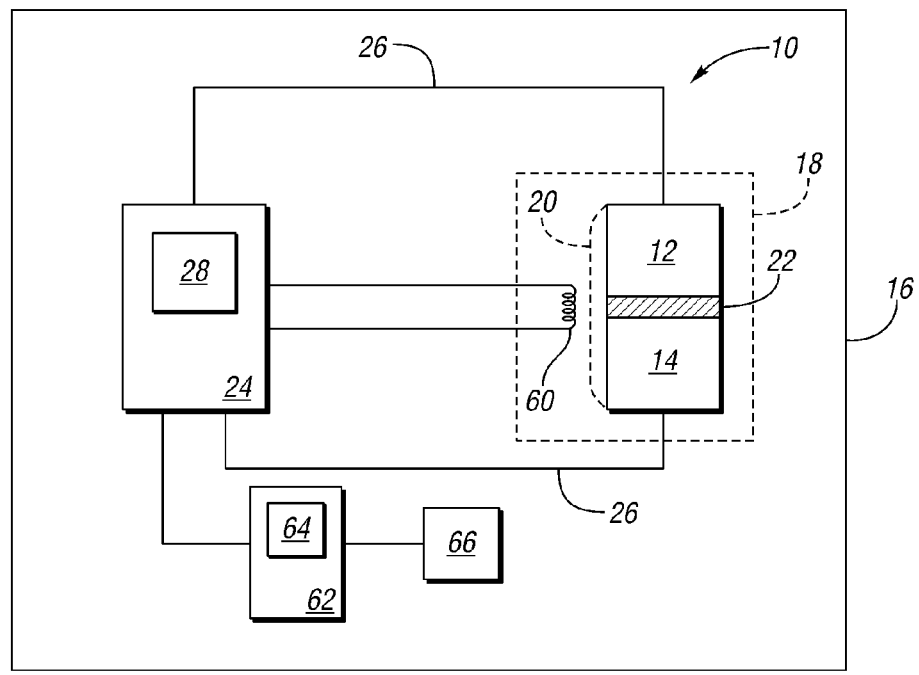
FIG. 1 is a schematic illustration of a system for indicating a likelihood of corrosion between two metals.

Referring to the drawings, wherein like reference numerals are used to identify like or identical components in the various views, FIG. 1 schematically illustrates a system 10 for indicating a likelihood of corrosion between a first metal 12 and a second metal 14. The system 10 may, for example, be used within an automotive vehicle 16 to detect whether a particular metal is at risk of corrosion, or whether corrosion has already begun to occur.

As schematically illustrated in FIG. 1, the metals 12, 14 may be provided in a local environment 18. Within the local environment 18, the metals 12, 14 may be subjected to various environmental conditions, including exposure to an electrolytic solution 20 that may at times contact each respective metal 12, 14. In an automotive vehicle context, for example, the electrolytic solution 20 may include water from the road that may splash onto the metals 12, 14. Alternatively, it may include rain that has run down the body of the vehicle 16, coating the various metals in the process.

In a particular configuration, electrically insulating material (i.e., a spacer 22) may be provided between the first and second metals 12, 14, and may be operative to electrically isolate the metals from each other. The spacer 22 may be an independent object, such as a rubber grommet, positioned between the first and second metals 12, 14. Alternatively, the spacer 22 may be a coating applied to one or both of the metals to isolate it from the other metal and the environment 18. For example, where the first metal 12 is a magnesium alloy and the second metal 14 is a steel alloy, the magnesium alloy may be either anodized or coated with an inert material prior to being assembled with the steel parts. As such, the anodized surface or inert coating may act as an electrically isolating spacer 22 between the magnesium and steel metals. When properly maintained, the spacer 22 may inhibit or discourage the creation of a galvanic couple between the two metals 12, 14. This may reduce the likelihood that one metal may corrode preferentially to the other metal. If the coating becomes compromised, local galvanic corrosion at the site of the damage may create a crevice. Any such crevice creation may further accelerate the corrosion attack in the coated panel, and may cause more coating to peel away, leading to further galvanic corrosion.

As schematically illustrated in FIG. 1, the system 10 may include a processor 24 electrically coupled with each of the first and second metals 12, 14. The coupling may be achieved, for example, through the use of wires 26. The processor 24 may be embodied as a server or a host machine, i.e., one or multiple digital computers or data processing devices, each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, and any required input/output (I/O) circuitry and devices, as well as signal conditioning and buffering electronics.

While shown as a single device in FIG. 1 for simplicity and clarity, the various elements of the processor 24 may be distributed over as many different hardware and software components, as may be required by the application. Individual control routines/instructions may be resident in the processor and may be stored in an associated tangible, non-transitory, electrically readable medium 28. The electrically readable medium 28 may be embodied as ROM, RAM, EEPROM, or Flash memory, or may be a combination of multiple different types. The instructions stored on the electrically readable medium 28 may be automatically executed by the various hardware components of the processor 24.

To detect a likelihood of corrosion between the adjacent metals 12,14, the processor 24 may be configured to monitor a complex impedance existing between the metals. The complex impedance may include both a real component and an imaginary component, where the real component may represent a resistance, and the imaginary component may represent a reactance. Resistance is commonly understood as a measure of a voltage drop across a circuit element per unit of current. Reactance is more commonly used as a measure of the opposition of a circuit element to a change of current. In alternating current (AC) circuits, the reactance may represent the phase change of a sinusoidal alternating current wave going through the circuit element. The complex impedance Z is often represented as the sum of the (real) resistance R and the (imaginary) reactance X, as shown in Equation 1.

$$Z=R+jX$$ Equation 1

In the arrangement shown in FIG. 1, the real component of the complex impedance (i.e., the resistance R) may indicate the quality of the electrical coupling between the first and second metals 12, 14. If an electrically insulating spacer 22 is provided between the metals, a relatively high resistance R may indicate that the spacer is intact and properly isolating the metals (i.e., it is providing a resistance to current flow between the metals). Conversely, a relatively low resistance R may indicate that the spacer has been damaged or compromised and may need to be replaced.

The imaginary component of the complex impedance (i.e., the reactance X) may indicate the presence of an electrolytic solution 20 in contact with both the first metal 12 and the second metal 14. As such, a relatively low reactance X may indicate the presence of an electrolytic solution 20, whereas a relatively high reactance X may indicate an absence of an electrolytic solution 20. These relationships may be summarized in Table 1.

TABLE 1

| case | R | X | Conclusion |
|---|---|---|---|
| 1 | High | High | Electrolyte absent; Spacer intact |
| 2 | High | Low | Electrolyte present; Spacer intact |
| 3 | Low | High | Electrolyte absent; Spacer compromised |
| 4 | Low | Low | Electrolyte present; Spacer compromised |

As used in Table 1, the states of "High" and "Low" may be defined according to particular characteristics of the system 10, including, for example, the metallurgical properties and/or physical relationship of the metals 12, 14. In an embodiment, the states of "High" and "Low" may be defined relative to one or more thresholds that may be determined through empirical/experimental observations. For example, a first threshold may be used to gauge whether the resistance R is sufficiently low to conclude that the insulating qualities/characteristics of the spacer 22 have begun degrading. Similarly, a second threshold may be used to gauge whether the reactance X is low enough to suggest the presence of an electrolytic solution 20. If either of these thresholds is crossed, the processor 24 may conclude that metals 12, 14 are subject to an increased likelihood of corrosion.

Figure 2:
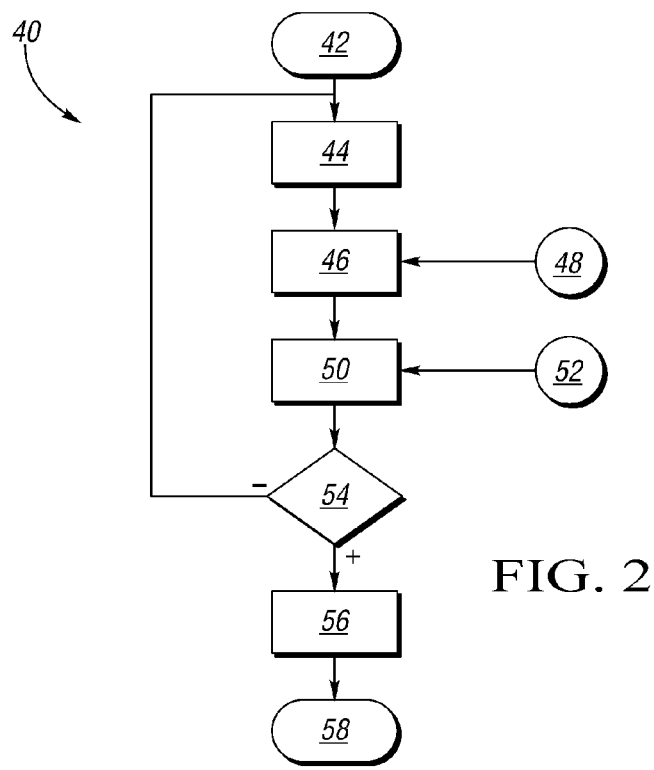
FIG. 2 is a flow diagram of a method for indicating a likelihood of corrosion between two metals.

As schematically illustrated in the flow diagram in FIG. 2, the processor 24 may be configured to test for the increased likelihood of corrosion by performing a method 40 that may be embodied by a sequence of instructions stored on the tangible, non-transitory, electrically readable medium 28 (shown in FIG. 1). As shown, the routine/method 40 may begin by initializing the routine at 42. Following initialization, the processor 24 may monitor a complex impedance between the first metal 12 and the second metal 14 in step 44. Such monitoring may occur by injecting an alternating current wave into one metal 12 and measuring the attenuation and phase shift of the wave via the other metal 14. As described above, the complex impedance may include both a real component and an imaginary component. In step 46, the processor 24 may compare the real component R of the complex impedance to a first threshold 48. Additionally, in step 50, the processor 24 may compare the imaginary component X of the complex impedance to a second threshold 52.

Once the components R, X have been compared to their respective thresholds 48, 52 in steps 46 and 50, the processor 24 may then indicate a likelihood of corrosion in step 54 if at least one of the real and imaginary components R, X are below their respective threshold. In an embodiment, the processor 24 may utilize a look up table in step 54, similar to that shown, for example, in Table 1, to draw conclusions about the metals and likelihood of corrosion. For example, in case 1 from the Table, where the spacer is intact, and no electrolyte is present, the likelihood for corrosion may be very low or non-existent. In cases 2 and 3, the likelihood of corrosion may be much higher since either an electrolyte is present, or the spacer is compromised. Finally, in case 4, it is likely that the metals may already be corroding.

If the processor 24 indicates a likelihood of corrosion in step 54, then in some configurations, the processor 24 may take a remedial action in step 56 to either reduce the likelihood of corrosion, or to alert a user or technician. For example, if the processor 24 indicates the presence of an electrolytic solution 20, the remedial action may be directed at removing the electrolytic solution. As shown in FIG. 1, this may include directly or indirectly energizing a resistive heating element 60 that may be located proximate to the first and second metals 12, 14. The resistive heating element 60 may be configured to heat the metals 12, 14 or environment 18 in a manner that may evaporate any solution 20 adjacent the metals. Conversely, if the processor 24 does not indicate a likelihood of corrosion, then it may repeat the analysis by obtaining a new complex impedance in step 44.

The remedial action of step 56 may additionally (or alternatively) include alerting a user or technician to the likelihood of corrosion through the use of stored diagnostic trouble codes and/or indicator lights. For example, if the processor 24 detects that the electrically insulating spacer 22 is compromised or damaged, the processor 24 may be configured to store a diagnostic trouble code in a memory 64 of an on board computer 62 provided within the vehicle 16. The diagnostic trouble code may include a register entry, flag, binary code, or other software representation that may be electronically stored and may indicate that the spacer 22 has been compromised. During service, for example, the diagnostic trouble code may be retrieved by a service technician, and may alert the technician that the spacer needs to be repaired or replaced. The processor 24 may additionally illuminate an indicator light 66, either directly, or through one or more on board computers 62, to alert a user of the vehicle 16 that a potential for corrosion may exist. Alternatively, the indicator light 66 may signify a need to have the vehicle 16 serviced. In an automobile context, the indicator light 66 may, for example, be located in the instrument panel of the automotive vehicle 16, and may be similar to a "service engine" light or "check oil" light.

Finally, the routine may end at 58 if, for example, a remedial action is performed, or the vehicle stops/shuts down. Alternatively, the routine/method 40 may continue to be performed indefinitely, such as via a continuous monitoring loop.

In a further embodiment, in step 44, the system may monitor a voltage potential between the metals 12, 14, in addition to the complex impedance. The magnitude of the potential difference may be used to gauge the reactivity of the metals and their natural inclination to corrode. A larger potential difference may enhance the magnitude of the risks/likelihood of corrosion that may be indicated in step 54.

FIGS. 3-4 illustrate potential applications of the detection system 10. FIG. 3 illustrates a hemmed closure 70 coupled to a processor 24, while FIG. 4 illustrates a wheel assembly 90 coupled to a processor 24. Within the manufacturing arts, "hemming" is a term that is used to refer to the process of rolling the edge of a workpiece over onto itself. This process is often performed with metals, such as sheet metal panels, to reinforce the edge, hide burrs or rough edges, conceal any sharp edges, or generally to improve the appearance of the panel. The hemming process may be used in an automotive vehicle to join two panels together to form a unitary structure. Exemplary hemmed structures may include vehicle doors, hoods, and trunk lids.

During the hemming process, a portion of an outer panel 72 may be folded over the inner panel 74 to such a degree that the outer panel 72 may apply a compressive load to the inner panel 74. In an embodiment, the compressive load may be sufficient to prevent the inner panel 74 from freely withdrawing from the hem 76 created by the outer panel 72. Additionally, an adhesive 78 may be provided between the two panels 72, 74 for additional restraint. Note that FIG. 3 has not been drawn to scale, and the gap between the inner and outer panels 72, 74 has been exaggerated for illustrative purposes. While this spacing should not be used to limit the scope of the current invention, typically the gap between the metal panels may be on the order of about 250 microns.

In certain configurations, the panels 72, 74 may be constructed from different metallic compositions. For example, as shown in FIG. 3, the inner panel 74 may be a high-strength magnesium alloy coated with an inert coating 80, while the outer panel 72 may be an aluminum body panel. Given that magnesium and aluminum have different potentials on the Anodic Index, there may be a natural inclination for the magnesium to corrode preferentially to the aluminum. As such, the inner panel 74 may comprise the first metal 12 and the outer panel 74 may comprise the second metal 14. If an electrolytic solution 20 were trapped in the hem (as shown), galvanic corrosion may occur if the inert coating 80 on the magnesium is compromised. Therefore, the processor 24 may be configured to monitor a complex impedance between the inner and outer panels 74, 72, to detect/indicate a likelihood of corrosion, if one should exist. Furthermore, the processor 24 may be configured to take remedial action if the likelihood of corrosion is indicated (such as, for example, evaporating any trapped electrolytic solution 20).

As shown in FIG. 4, in another embodiment, the system 10 may be used to detect a likelihood of corrosion in an automotive wheel assembly 90, such as when the wheel assembly is subjected to a fluid bath (e.g., driving through a puddle). As shown, the assembly 90 may include a wheel 92 made from a magnesium alloy and coated with an inert material 94, along with a steel brake disk 95, and a steel axle 96. If the electrolytic fluid were to cover the wheel 92, or get trapped in any junctures (e.g., the wheel-axle juncture, or a screw juncture between the wheel and steel lug-bolt (not shown)), the magnesium wheel 92 may be inclined to act as a first metal 12 in a galvanic couple and the brake disk 94, axle 96, or steel lug-bolt may act as the second metal 14. As such, the processor 24 may be configured to monitor a complex impedance between the wheel 92 and axle 96 (or other components), and indicate whether a likelihood of corrosion may exist. If so, the processor 24 may be configured to take remedial action to reduce the likelihood of corrosion, or to alert a user or technician. While FIGS. 3-5 illustrate several applications of the system 10, they should be viewed as illustrative examples, and should not be construed to limit the invention.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A vehicle sub-assembly comprising:
a first metal;
a second metal adjacent the first metal; and
a processor electrically coupled to each of the first and the second metals; the processor configured to:

monitor a complex impedance between the first metal and the second metal, the complex impedance including a real component and an imaginary component;
compare the real component of the complex impedance to a first threshold;
compare the imaginary component of the complex impedance to a second threshold; and
indicate a likelihood of corrosion if at least one of the real and imaginary components are below their respective threshold.

2. The vehicle sub-assembly of claim 1, wherein the processor is configured to indicate the presence of an electrolytic solution in contact with the first and second metals if the imaginary component of the monitored complex impedance is below the second threshold.

3. The vehicle sub-assembly of claim 2, wherein the processor is configured to take remedial action to remove the electrolytic solution if the presence of the solution is indicated.

4. The system sub-assembly of claim 3, wherein the remedial action includes energizing a resistive heating element located proximate to the first and second metals.

5. The vehicle sub-assembly of claim 1, further comprising an electrically insulating material provided between the first metal and the second metal; and, wherein the processor is configured to indicate damage to the insulating material if the real component of the monitored complex impedance is below the first threshold.

6. The vehicle sub-assembly of claim 1, wherein the processor is configured to indicate a likelihood of corrosion by storing a diagnostic trouble code in a memory of an on board computer provided within the vehicle or illuminating an indicator light within the vehicle.

7. The vehicle sub-assembly of claim 1, wherein the first metal and second metal are disposed in a hemmed arrangement.

8. The vehicle sub-assembly of claim 1, wherein at least one of the first and second metals comprises a vehicle wheel.

9. The vehicle sub-assembly of claim 1, wherein the processor is further configured to monitor an electrical potential between the first and second metals.

10. A system for indicating a likelihood of corrosion between a first metal and a second metal, the system comprising:
a processor electrically coupled to each of the first and second metals, the processor including a tangible, non-transitory, electrically readable medium with instructions stored therein;
the processor configured to execute the instructions to:
monitor a complex impedance between the first and second metals, the complex impedance including a real component and an imaginary component;
compare the real component of the complex impedance to a first threshold;
compare the imaginary component of the complex impedance to a second threshold; and
indicate a likelihood of corrosion if at least one of the real and imaginary components are below their respective threshold.

11. The system of claim 10, wherein the processor is configured to indicate the presence of an electrolytic solution in contact with the first and second metals if the imaginary component of the monitored complex impedance is below the second threshold.

12. The vehicle of claim 11, wherein the processor is configured to take remedial action to remove the electrolytic solution if the presence of the solution is indicated.

13. The system of claim 12, wherein the remedial action includes energizing a resistive heating element located proximate to the first and second metals.

14. The system of claim 10, wherein the processor is further configured to store a diagnostic trouble code within an electrically readable medium if a likelihood of corrosion is indicated.

15. A method of detecting a likelihood of corrosion between a first metal and a second metal, the method comprising:
monitoring a complex impedance between the first and second metals, the complex impedance including a real component and an imaginary component;
comparing the real component of the complex impedance to a first threshold;
comparing the imaginary component of the complex impedance to a second threshold; and
indicating a likelihood of corrosion if at least one of the real and imaginary components are below their respective threshold.

16. The method of claim 15, further comprising indicating the presence of an electrolytic solution if the imaginary component of the monitored complex impedance is below the second threshold.

17. The method of claim 16, further comprising taking remedial action to remove the electrolytic solution if the presence of the solution is indicated.

18. The method of claim 17, wherein taking remedial action includes energizing a resistive heating element located proximate to the first and second metals.

19. The method of claim 15, further comprising monitoring an electrical potential between the first and second metals.

20. The method of claim 15, wherein indicating a likelihood of corrosion includes storing a diagnostic trouble code in a memory of an on board computer provided within the vehicle.

* * * * *